US008164333B2

(12) United States Patent
Rugar et al.

(10) Patent No.: US 8,164,333 B2
(45) Date of Patent: Apr. 24, 2012

(54) MAGNETIC RESONANCE FORCE DETECTION APPARATUS AND ASSOCIATED METHODS

(75) Inventors: Daniel Rugar, Los Altos, CA (US); Harry Jonathon Mamin, Palo Alto, CA (US); Tjerk Hendrik Oosterkamp, Leiden (NL)

(73) Assignee: International Business Machines Corporation, Armonk, NY (US)

( * ) Notice: Subject to any disclaimer, the term of this patent is extended or adjusted under 35 U.S.C. 154(b) by 301 days.

(21) Appl. No.: 12/473,725

(22) Filed: May 28, 2009

(65) Prior Publication Data
US 2010/0301854 A1 Dec. 2, 2010

(51) Int. Cl.
*G01V 3/00* (2006.01)
(52) U.S. Cl. ...................................... 324/307
(58) Field of Classification Search ........... 324/300–322
See application file for complete search history.

(56) References Cited

U.S. PATENT DOCUMENTS

| 5,266,896 | A | 11/1993 | Rugar et al. |
| 5,619,139 | A | 4/1997 | Holczer et al. |
| 5,825,843 | A * | 10/1998 | Kobayashi ............... 378/20 |
| 6,100,687 | A | 8/2000 | Weitekamp et al. |
| 6,181,131 | B1 | 1/2001 | Bruland et al. |
| 6,522,908 | B1 * | 2/2003 | Miyashita et al. ......... 600/409 |
| 6,683,451 | B1 | 1/2004 | Moore et al. |
| 6,961,606 | B2 * | 11/2005 | DeSilets et al. .......... 600/415 |
| 7,254,438 | B2 * | 8/2007 | DeSilets et al. .......... 600/427 |
| 7,400,144 | B2 | 7/2008 | Tsuji et al. |
| 7,403,008 | B2 | 7/2008 | Blank et al. |
| 7,574,327 | B2 | 8/2009 | de Roover et al. |
| 7,847,549 | B2 * | 12/2010 | Takahashi et al. ......... 324/307 |
| 7,924,007 | B2 * | 4/2011 | Arnold et al. ............. 324/309 |
| 2009/0242764 | A1 | 10/2009 | Xi et al. |

FOREIGN PATENT DOCUMENTS

| EP | 0 979 424 A1 | 12/1997 |
| EP | 0 726 444 B1 | 10/2001 |
| EP | 1 830 172 A2 | 9/2007 |
| WO | WO 00/73821 A1 | 12/2000 |
| WO | WO 2007/044076 A2 | 4/2007 |

(Continued)

OTHER PUBLICATIONS

Degen, C.L., et al., "Nanoscale Magnetic Resonance Imaging,"*PNAS*, 106(5): 1313-1317 (2009).
Eberhardt, K.W., et al., "Fast Magnetic Resonance Force Microscopy with Hadamard Encoding," *Phys. Rev. B, Condens. Matter Mater. Phys.*, 76(18): 180405-1-4 (2007).

(Continued)

*Primary Examiner* — Dixomara Vargas
(74) *Attorney, Agent, or Firm* — Hamilton, Brook, Smith & Reynolds, P.C.

(57) ABSTRACT

A magnetic resonance force detection apparatus, comprising a sample carrier for carrying a sample to be tested, a magnetic field source and a support for supporting either the sample carrier or the magnetic field source. The magnetic field source is configured to expose the sample to a magnetic field by simultaneously providing a plurality of volumes in which the magnetic field is configured to cause the spins of one or more nuclei or electrons in the sample to flip, and wherein the flipping of spins exerts a force on the support. The apparatus also comprises a support displacement measuring sensor configured to measure the displacement of the support and generate a signal representative of the displacement of the support, and a processor configured to process the signal representative of the displacement of the support in order to determine a component of the displacement of the support caused by one or more of the plurality of volumes.

16 Claims, 3 Drawing Sheets

FOREIGN PATENT DOCUMENTS

WO    WO 2008/027601 A2    3/2008

OTHER PUBLICATIONS

Fong, et al., "Manipulating Spins by Cantilever Synchronized Frequency Modulation: A Variable Resolution Magnetic Resonance Force Microscope," *Appl. Phys. Lett.*, 93(1):012506-1-3 (2008).

Berman, et al., "Random Spin Signal in Magnetic Resonance Force Microscopy," *Phys. Lett. A*, 318(16): 584-591 (2003).

Kempf, et al., "Nanoscale Fourier-Transform Imaging with Magnetic Resonance Force Microscopy," *Phys. Rev. Lett.*, 90(8): 087601-1-4 (2003).

SangGap, et al., "Magnetic Resonance Force Microscopy in Fast-Relaxing Spins Using a Frequency-Modulation Mode Detection Method," *Nanotechnology*, 18(37): 375505-375510 (2007).

Volodin, et al., "Piezoresistive Mechanical Detector for Magnetic Resonance Force Microscopy," *Rev. Sci. Inst.*, 76(6): 63705-1-5 (2005).

Wago, et al., "Magnetic Resonance Force Detection and Spectroscopy of Electron Spins in Phosphorus-Doped Silicon," *Rev. Sci. Inst.* (68(4): 1823-6 (1997).

Eberhardt, K.W., et al., "Two-dimensional Magnetic Resonance Force Microscopy Using Full-volume Fourier and Hadamard Encoding," *Physical Review B* 78:214401-1-214401-5 (2008).

Ren, R., et al., "Nuclear Spin Magnetic Resonance Force Microscopy Using Slice Modulation," *Physics Letters A* 372:c1-c4 (2008).

UK IPO Search Report from Application No. GB0913555.9, dated: Dec. 10, 2009.

\* cited by examiner

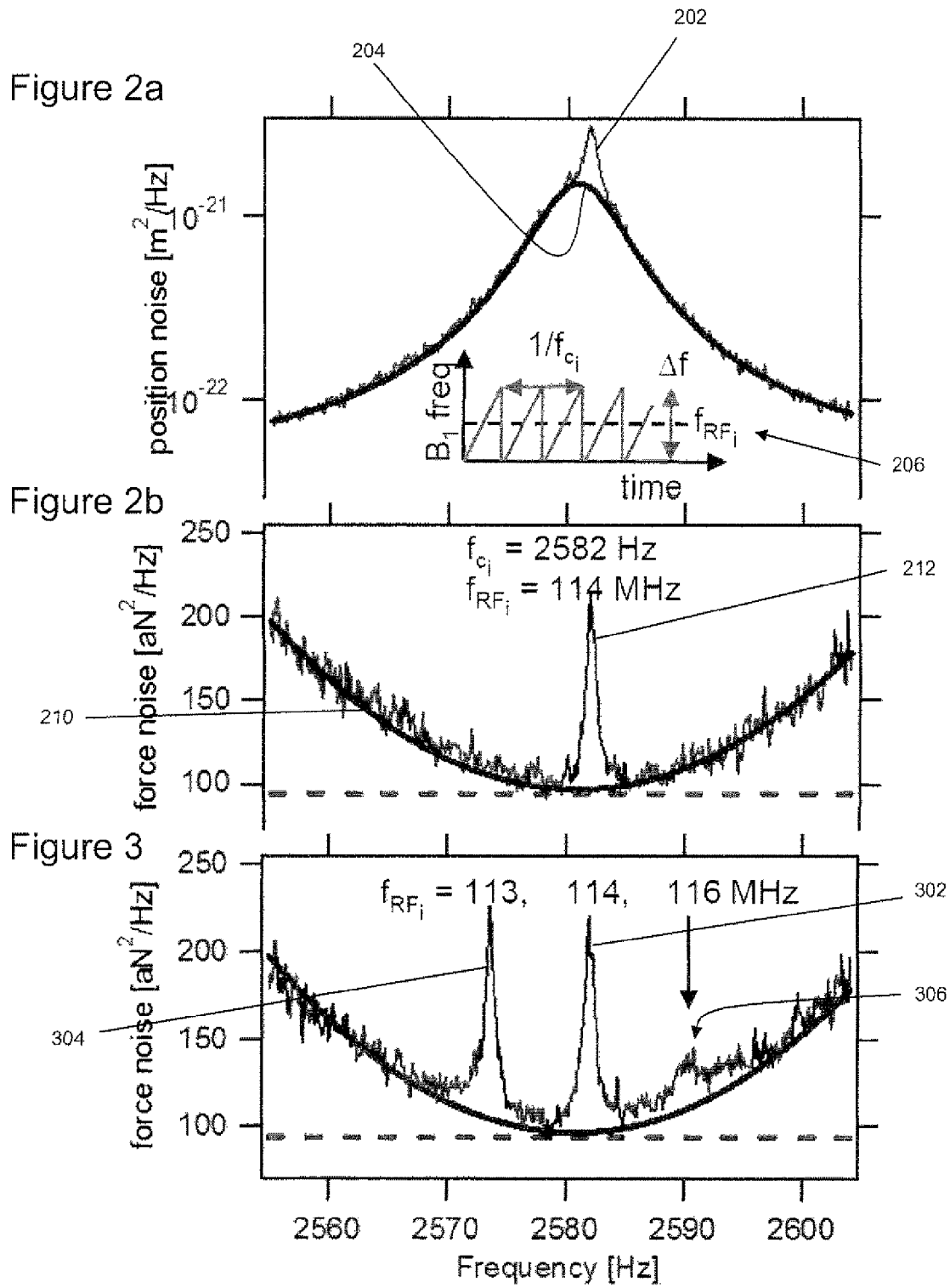

MAGNETIC RESONANCE FORCE DETECTION APPARATUS AND ASSOCIATED METHODS

BACKGROUND

The present disclosure relates to a magnetic resonance force detection apparatus, and associated methods for using such apparatus.

Magnetic resonance force microscopy (MRFM) involves the combination of magnetic resonance imaging (MRI) with the techniques of scanning probe microscopy (SPM). Essentially, the technique relies on detecting the tiny force resulting from the modulation or flipping of nuclear or electron spins. Recently this has led to the demonstration of nuclear spin imaging of a virus particle with a spatial resolution of 4 nm. Most recently, the sensitivity has been improved by increasing the magnetic field gradient provided by an integrated nanomagnetic tip near the nuclear spins and a "microwire" RF source. Yet, because of the small forces involved, relatively long averaging times are required to be able to distinguish the forces due to the controlled manipulation of the nuclear spins from the thermal forces acting on a cantilever that is used for force detection.

U.S. Pat. No. 5,266,896 describes using a mechanical cantilever to detect the modulation of nuclear or electron spin magnetism in a sample where a high frequency magnetic field is used to drive spin resonance and thereby control the modulation or reversal of the spins in the sample.

The paper entitled "Nanoscale Magnetic Resonance Imaging" by C. L. Degen, M. Poggio, H. J. Mamin, C. T. Rettner and D. Rugar, dated 11 Nov. 2008 and published in the PNAS (Proceedings National Academy of Sciences) journal, describes converting measured magnetic force data into a three-dimensional map of nuclear spin density, taking advantage of the unique characteristics of the "resonant slice" that is projected outwards from a nanoscale magnetic tip. Since the field from the magnetic tip is a strong function of position, the resonance is confined to a thin, approximately hemispherical "resonant slice" that extends outwards from the tip. The field gradient at the resonant slice can exceed $4 \times 10^6$ T/m at a distance of 25 nm from the tip, resulting in a slice thickness that is as thin as a few nanometers. The spin signal is measured as the magnetic tip is mechanically scanned with respect to the sample in a three-dimensional raster pattern, yielding a map of the spin signal as a function of tip position.

The paper entitled "Fast magnetic resonance force microscopy with Hadamard encoding" by Kai W. Eberhardt, Christian L. Degen, and Beat H. Meier dated 26 Nov. 2007 (PHYSICAL REVIEW B 76, 180405(R) (2007)) discloses a spatial encoding technique for magnetic resonance force microscopy that allows for a much enhanced image acquisition rate. The technique uses multiplexing, based on spatial Hadamard encoding, to acquire several slices of the image simultaneously and at an undiminished signal-to-noise ratio.

The listing or discussion of a prior-published document or any background in this specification should not necessarily be taken as an acknowledgement that the document or background is part of the state of the art or is common general knowledge. One or more aspects/embodiments of the present disclosure may or may not address one or more of the background issues.

SUMMARY

According to a first embodiment, there is provided a magnetic resonance force detection apparatus, comprising:

a sample carrier for carrying a sample to be tested;

a magnetic field source;

a support for supporting either the sample carrier or the magnetic field source;

wherein the magnetic field source is configured to expose the sample to a magnetic field by simultaneously providing a plurality of volumes in which the magnetic field is configured to cause the spins of one or more nuclei or electrons in the sample to flip, and wherein the flipping of spins exerts a force on the support;

a support displacement measuring sensor configured to measure the displacement of the support and generate a signal representative of the displacement of the support; and a processor configured to process the signal representative of the displacement of the support in order to determine a component of the displacement of the support caused by one or more of the plurality of volumes.

Simultaneously providing the plurality of volumes can enable a plurality of MRFM measurements to be taken at the same time, thereby decreasing the time required to process a sample and providing an efficient apparatus for performing magnetic resonance force detection in terms of at least power consumption.

The term "simultaneously" can mean that at least two volumes are addressed by the magnetic field source at the same instance in time, and this may be known as generating a plurality of resonant slices with a radiofrequency (RF) magnetic field. In some embodiments, each of the plurality of volumes is constantly addressed for the entire duration of a measurement that is being taken. The volumes may be configured such that the magnetic field that is present in that volume causes nuclear magnetic resonance of nuclei in the volume, and for this reason a volume may be known as a "resonant slice".

The flipping of spins may exert a time varying force on the support. That is, the direction and or magnitude of the force exerted by the flipping of spins may change over time. In this way, the displacement of the support also changes over time such that a time varying signal representative of the displacement of the support can be processed in order to determine a component of the displacement of the support caused by one or more of the plurality of volumes.

It will be appreciated that the volumes in which the magnetic field is configured to cause the spins of one or more nuclei to flip, can be a volume in free-space at a location relative to the magnetic field source in accordance with characteristics of the magnetic field generated, including a frequency of oscillation of the magnetic field. The volume can be located such that at least a region of the sample to be measured is located in the volume such that the magnetic field in that volume can cause spins to flip.

The processor may be configured to simultaneously process the received signal in order to determine a component of the displacement of the support caused by each of the individual volumes. Fourier transform processing may be used to identify displacements of the support that are occurring at different frequencies. In this way, signal processing can be used to determine the displacement of the support, and hence the force exerted on the support by the spins flipping, caused by each of the volumes/resonant slices at the same time.

The support may be a cantilever, which may be an ultra-sensitive cantilever, and the sample may be attached to a sample carrier associated with the free end of the cantilever. In other embodiments, the magnetic field source may be associated with a free end of the cantilever.

The magnetic field source may be any device that can generate a magnetic field gradient. The magnetic field source may be controllable, such that the frequency modulation and/or amplitude modulation of the magnetic field can be controlled in order to provide resonant slices that cause the spins of nuclei of a specific species to flip at a desired flipping frequency. The flipping frequency may be selected such that it causes the support to oscillate at a frequency at which the additional support motion is distinguishable from the motion of the support caused by environmental conditions. Environmental conditions can include thermal vibrations of the support and detection noise, which can be independent of frequency.

In some embodiments the flipping frequency is selected so that it is close to the resonant frequency of the support, as it may be possible to provide sensitive readings of the displacement of the support for motion at such frequencies. However, it will be appreciated that any other flipping frequency may be used.

The magnetic field source may comprise a radiofrequency (RF) magnetic field source, wherein the RF magnetic field source is configured to provide a magnetic field comprising the superposition of a plurality of radiofrequency components. In some embodiments, the magnetic field source may comprise a magnetic tip, a microwire and a current source, wherein the current source may be configured to provide the microwire with a current comprising the superposition of a plurality of oscillating current components such that the magnetic tip associated with the microwire generates the required magnetic field. In such embodiments, the magnetic tip may be considered as the component that provides the magnetic field, and therefore any reference to a "magnetic field source" herein can be considered as a reference to "magnetic" according to some embodiments. In embodiments where the magnetic field source is supported by the support, it may be only the magnetic tip, and possibly not the microwire, that is supported by the support.

The current components may be oscillating at a radiofrequency (RF), which can include the range 3 Hz to 300 GHz. In other embodiments, the RF magnetic field can be generated by a magnetic particle that is moved (such as shaken) up and down, for example. This concept can also be extended to a magnetic tip that generates a permanent/background magnetic field for embodiments that have a background field. This could be provided by an electro magnet in some embodiments.

Each of the plurality of radiofrequency components can be configured to cause the magnetic tip to address a volume in which the magnetic field causes the spins of one or more nuclei or electrons to flip. The location of the volume relative to the magnetic tip can be set by the frequency of a radiofrequency component and/or can be set by adjusting characteristics of a background magnetic field.

The radiofrequency components may each be at a frequency that causes magnetic resonance of a specific spin species in the corresponding volume, for example, nuclear magnetic resonance of a specific nuclear spin species. In this way the presence of that specific nuclear species can be determined for the volume/resonant slice.

The radiofrequency components may be modulated in order to cause the spins to flip at a different frequency for each volume/resonant slice that corresponds to a different radiofrequency component. Each radiofrequency component may be configured to cause the spin of a specific nuclear species to flip in a specific resonant slice, at a specific flipping frequency that can be distinguished from the flipping frequencies caused by other resonant slices. The radiofrequency components may be frequency and/or amplitude modulated for example.

The radiofrequency components may each be modulated in order to cause the spins to flip at a frequency that is at, or close to, the resonant frequency of the support. "At, or close to" may be within 5, 10, 15, 20 Hz (for example) of the resonant frequency of the support. "Close to" may be close enough to the resonant frequency of the support that the displacement of the support caused by the flipping of spins excites the support sufficiently for its motion to be distinguishable from thermal or detection noise. Also, the frequency at which the spins flip (flipping frequency), may be set such that the displacement of the support caused by spin flips in one volume are distinguishable from the displacement of the support caused by spin flips in other volumes.

The support may be configured to be displaceable in a plurality of dimensions or modes in response to the flipping of spins. The support may have a geometry that provides for this. Each of the plurality of dimensions may have its own resonant frequency, and the spin flips of a first volume may be configured to flip at a frequency corresponding to the support resonant frequency in a first dimension or mode, and a second volume may be configured to flip at a frequency corresponding to the support resonant frequency in a second dimension or mode. In this way, interference between the measurement of displacements/forces caused by different volumes can be reduced. Also, different modes having different point spread functions can be used.

One or more of the modes of motion of the support can be in the same or different dimensions. In some embodiments the resonant motion of the support can take an elliptical or other non-linear path.

The support displacement measuring sensor may comprise a fibre-optic interferometer that may be configured to receive laser light reflected from a paddle associated with the support. Such a support displacement measuring sensor may provide sufficiently accurate measurements.

According to a further embodiment, there is provided a method of performing magnetic resonance force detection for a sample using a magnetic field source, wherein either the sample or the magnetic field source is supported by a support, the method comprising:
  simultaneously providing a plurality of volumes in which a magnetic field is provided to cause the spins of one or more nuclei or electrons in the sample to flip, wherein the flipping of spins exerts a force on the support;
  measuring the displacement of the support; and
  determining a component of the displacement of the support caused by an individual volume.

In some embodiments both the sample and the magnetic field source may be supported by a support.

The volume in which the magnetic field is configured to cause the spins of one or more nuclei or electrons to flip may be a resonant slice. The volumes may be distinct volumes that encompass different regions of the sample, or may be overlapping volumes.

The method may comprise simultaneously providing two volumes, wherein: a first volume is configured to cause the spins of one or more nuclei of a first nuclear species in the sample to flip; and a second volume is configured to cause the spins of one or more nuclei of a second nuclear species in the sample to flip. In this way, the presence of a plurality of different nuclear species in a sample can be measured simultaneously.

The first and second volumes may be at least partially coincident, and may be entirely coincident. This can provide an advantage in that the presence of different nuclear species in a single volume can be determined at the same time. In other embodiments, the first and second volumes may be non-coincident.

There may be provided a computer program configured to configure any apparatus disclosed herein, or perform any method disclosed herein. The computer program may be stored on a computer readable medium such as a disc or computer memory, or may be encoded as a transient signal, such as a download from a network, including an internet download.

The present disclosure includes one or more corresponding aspects, embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 2a and 2b illustrate graphically the results of prior art MRFM measurements;

FIG. 3 illustrates graphically the results of MRFM measurements according to an embodiment;

DETAILED DESCRIPTION OF THE PREFERRED EMBODIMENTS

A description of example embodiments of the invention follows.

The teachings of all patents, published applications and references cited herein are incorporated by reference in their entirety.

One or more embodiments described herein relate to a magnetic resonance force detection apparatus that simultaneously addresses a plurality of magnetic field volumes/ "slices" in order to simultaneously flip the spin of nuclei or electrons in the plurality of volumes/"slices". A "slice" may also be known as a "resonant slice" and can represent a relatively thin volume in which a magnetic field is generated that excites the nuclear magnetic resonance (NMR) of a certain nuclear/atomic species or electron spin resonance (ESR) of electrons in that volume. The resonant slice can be a relatively thin volume, as little as a few nanometers, due to the magnetic field being a strong function of position relative to a magnetic field source.

The location of the resonant slice for a part of a sample can be controlled by setting the frequency of the magnetic field source such that a nuclear magnetic resonant frequency is provided at the desired part of the sample, by changing the strength of the background magnetic field and by changing the relative positions of the sample and magnetic tip.

The spin of nuclei or electrons in each of the resonant slices is controlled such that nuclei or electrons in different slices flip at different flipping frequencies. That is, the flipping frequency of a first resonant slice is different from the flipping frequency of a second resonant slice, etc. In this way, signals representative of the spins flipping simultaneously in different resonant slices can be distinguishable from each other. It can be advantageous for each of the flipping frequencies to be near the resonant frequency of a support such that the forces caused by the spins flipping can be easily distinguished from detection noise observed by a displacement sensor of a support to which the sample or magnetic field source are connected.

Simultaneously generating the plurality of resonant slices can enable the total processing time for imaging a sample, such as a nanoscale biological structure, for example a protein, to be greatly reduced as a plurality of data measurements can be made simultaneously. Embodiments can enable more data to be taken in the same sampling time when compared with prior art apparatus.

One or more embodiments described herein can make it possible to perform several MRFM experiments in parallel. For example, one can simultaneously measure different nuclear species and/or measure spins at different locations, which can allow more data to be taken in the same amount of averaging time.

Although the following description relates primarily to the flipping of spins of nuclei, it will be appreciated that the same principles apply to the flipping of electron spins and that the invention is equally applicable to the spin of nuclei and electrons.

Figure 1:
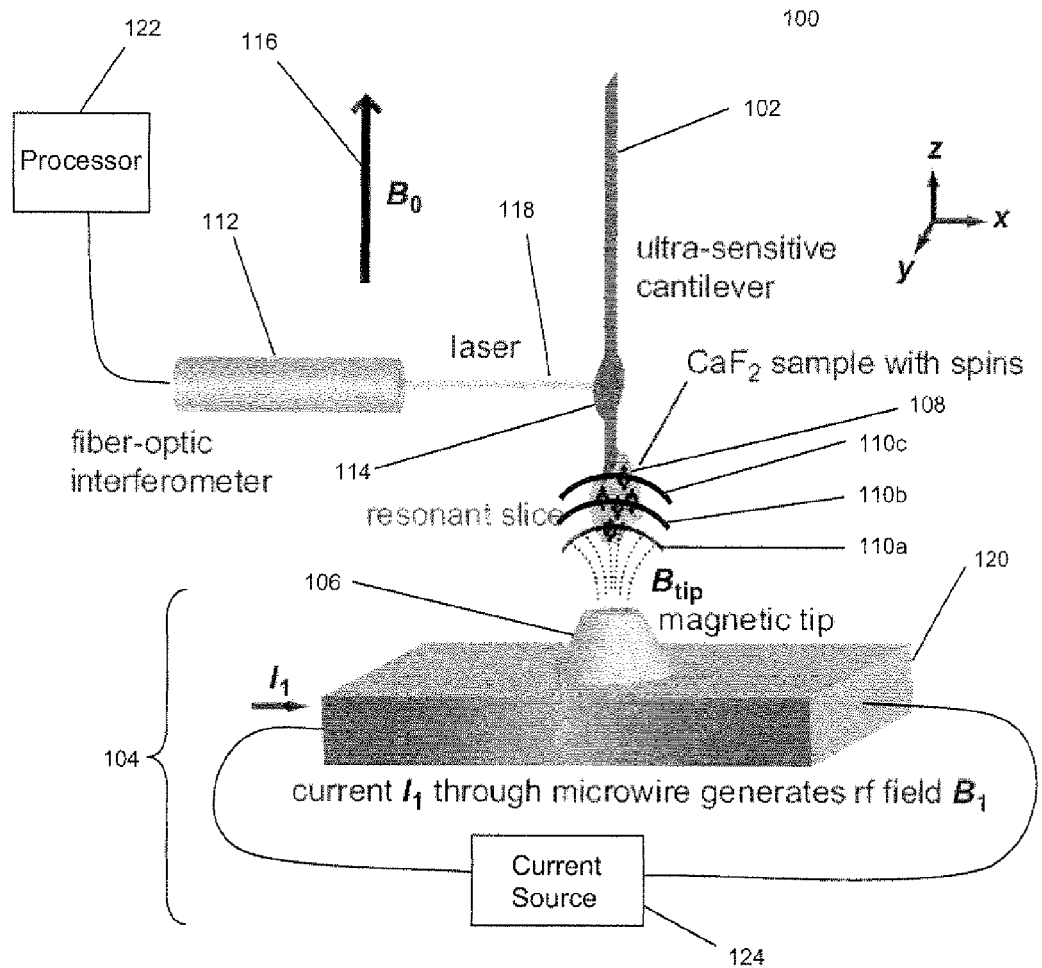
FIG. 1 illustrates an apparatus according to an embodiment.

FIG. 1 illustrates a magnetic resonance force detection apparatus 100 according to an embodiment of the present invention. The magnetic resonance force detection apparatus 100 can be used for imaging nanoscale biological structures, in some embodiments imaging down to the scale of individual molecules, and may be known as a sample-on-cantilever configuration.

The apparatus 100 comprises a support 102, which in this embodiment is an ultra-sensitive cantilever, for supporting a sample 108. The sample 108 is attached to the free end of the support 102 which can be considered a sample carrier.

The apparatus 100 may be located in a fixed background magnetic field, also known as an external magnetic field $B_o$, although in other embodiments the external magnetic field may not be necessary. The external background field $B_o$ causes the spin of nuclei to be aligned in the absence of other magnetic fields, particularly in the absence of a resonant slice 110 as will be discussed below.

Located near the sample 108 is a magnetic field source 104 that is configured to simultaneously expose the sample 108 to a plurality of "resonant slices" of magnetic field 110, 110b, 110c. The resonant slices 110 are volumes in which the magnetic field is configured to cause the spins of one or more nuclei in the sample 108 to flip. Each of the resonant slices 110 is generated by an oscillating component of a total current flowing $I_1$ through a microwire 120 as described in more detail below, and this means that each of the resonant slices flips the spins that are in that resonant slice.

In some embodiments the current flowing through the microwire 120 is the sum of a number of frequency modulated and amplitude modulated currents such that each of the resonant slices sweeps through a small region of space. This may be known as a "breathing" resonant slice. The maximum thickness of a breathing resonant slice is defined by the bandwidth of the modulated RF signal.

The RF magnetic field causes the spin of nuclei in that resonant slice having a corresponding resonant frequency to flip.

In other embodiments, instead of using frequency modulation, the RF signal can be the sum of many π-pulses that address spins in different resonant slices. A π-pulse is a form of amplitude modulation that provides an RF signal with a high amplitude for a period of time in order to flip the spin. A π-pulse can be considered as a short sharp pulse that is used to flip the spin of nuclei by 180°, and the amplitude and duration of the pulse are set in order to achieve this.

In certain embodiments, the polarization of the spins is due to the naturally occurring $\sqrt{N}$ statistical component of the spin ensemble, where N is the number of spins in the measurement volume/resonant slice. The spins can be flipped for a period of time such that statistics can be used to obtain an averaged value for N.

The application of a resonant slice 110 causes nuclei to flip. The magnetic field that is present in a resonant slice is at the nuclear magnetic resonance frequency of the nuclei that are to be flipped. That is, the magnetic field $B_{tip}$ induces magnetic resonance in a thin "resonant slice" of spins where the Larmor resonance condition is fulfilled.

It will be appreciated that spins flipping exert a force on the cantilever 102 to which the sample 108 is attached.

The force applied to the cantilever 102 by the spins of nuclei in the sample 108 flipping, causes the cantilever 102 to be displaced, and this displacement can be detected by a support displacement measuring sensor. In this embodiment, the cantilever 102 is designed such that it is much wider than it is thick, and therefore the cantilever 102 is displaced/flexed in a direction that is perpendicular to its thickness. The resonant frequency of the cantilever 102 in this dimension is known, and the magnetic field is controlled in order to flip the spins of the nuclei at a frequency that causes the cantilever 102 to resonate in the desired dimension.

The support displacement measuring sensor in this embodiment comprises a fibre-optic interferometer 112 which focuses laser light 118 on to a paddle 114 associated with the cantilever 102. The paddle 114 is near the end of the cantilever 102 to which the sample 108 is attached. The laser light 118 is reflected back to the fibre-optic interferometer 112 by the paddle 114, such that the displacement of the cantilever can be determined and a signal representative of the displacement of the cantilever can be generated.

In this embodiment, the fibre-optic interferometer 112 is in communication with a processor 122, such that the fibre-optic interferometer 112 can provide the processor 122 with one or more signals representative of the displacement of the cantilever 102.

The processor 122 is configured to process the received signal(s) in order to determine one or more of the components of the total displacement of the cantilever 102 that is caused by each of the individual resonant slices 110a, 110b, 110c. The one or more components are at different frequencies (as described in more detail below, particularly with reference to FIG. 3), and therefore a Fourier transform can be applied to a signal representative of the displacement of the cantilever 102 in order for components at different frequencies to be identified and attributed to the resonant slice 110 that caused them. In this way, the forces/displacements caused by each of the resonant slices 110 can be simultaneously determined.

In this embodiment, the processor 122 uses a digital lock-in to retrieve the multiple frequency components from the overall movement of the cantilever 102. Operation of the processor 122 may differ from that in the prior art, in which a regular lock-in operation is used to process only movements that are detected at the resonant frequency of the cantilever 102.

In some embodiments a trigger can be used that is associated with the plurality of RF current signals that are flowing through the microwire 120. In this way, the processor 122 can know the starting phase and frequency for sine and cosine waves that should be used for each of the different components of the movement of the support. Each of the sine and cosine waves can then be multiplied by the deflection signal generated by the support displacement measuring sensor in order to generate lock-in signals that can be low-pass filtered in order to obtain an in-phase and out-of-phase lock-in signal for each component of movement of the support.

According to certain embodiments, a single centre-frequency RF signal can be used for each resonant slice, and the magnetic tip and/or sample 108 can be moved relative to each other in order to expose different regions of the sample to the resonant slice. In this way, a full three-dimensional image of the sample 108 can be built up as the location of the resonant slices 110 are moved throughout the sample 108. When processing the signals indicative of the movement of the support 102 received at the processor 122, a deconvolution operation that uses information relating to the location of the resonant slice 110 in the sample 108 can be used to generate a spin density as a function of the three-dimensions X, Y and Z.

In other embodiments, lock-in can be performed with square waves instead of sine and cosine waves, for example.

In this embodiment, the magnetic field source 104 comprises a "microwire" 120, which is a very thin metallic wire through which a current is passed. A magnetic tip 106 sits on the microwire 120, and generates a strong and homogenous magnetic field $B_{tip}$ in accordance with the current that is passing through the microwire 120. In this embodiment, the current $I_1$ passing through the microwire 120 consists of the superposition of a plurality of radiofrequency (RF) signals at different frequencies/, wherein each of the individual RF signals causes a separate resonant slice 110a, 110b, 110c to be generated by the magnetic tip 106.

Raising or lowering the external field $B_0$ shifts the resonant slice position up or down, allowing spins further from or closer to the tip to be selectively addressed, respectively. Likewise, raising or lowering the frequency of the RF magnetic field at a fixed external field $B_0$, shifts the resonant slice position down or up, respectively. The external field $B_o$ and/or the RF magnetic field may be adjusted in combination with, or instead of, adjusting the relative physical location of the magnetic tip 106 and sample 108.

The frequency of the RF signals may be modulated using any type of oscillating function, including a sawtooth waveform, a triangular wave, a trapezoidal function, or any other function/waveform that causes resonant slices to be provided. One way of considering the nature of the resonant slices due to the RF signals, is that the thickness of the resonant slice changes as the associated modulated component of the current $I_1$ through the microwire 120 changes. The period/frequency at which the spins are allowed to flip is set so as to be near the resonant frequency of the cantilever 102, such that forces generated by the flipping can be distinguished from detection noise of the cantilever 102.

In some embodiments, one or both of the amplitude and the frequency of the current signals $I_1$ generated by the current source 124 may be modulated in order to generate resonant slices of magnetic field that are suitable for use with the present invention. In some embodiments, adiabatic passage may be used, while in other embodiments π-pulses may be used or yet other spin manipulations may be used.

The simultaneous generation of the resonant slices 110 causes nuclear spins to simultaneously flip in each of the resonant slices 110 at different frequencies. That is, each of the resonant slices 110 has its own flipping frequency. The flipping of the spins in each of the resonant slices 110 imparts a force on the cantilever 102, and the forces generated by each of the separate resonant slices are also at different frequencies in accordance with the different flipping frequencies. In this way, displacement of the cantilever 102 can be measured and processed to separate out the movement of the cantilever 102 caused by different frequencies of the movement of the cantilever 102, for example using a Fourier transform, in order to determine the force generated by each individual resonant slice.

There will now be described specific details of an experiment made with an apparatus similar to the apparatus 100 of FIG. 1. For this experiment, the cantilever 102 is a single crystal silicon cantilever, and is 120 µm long, 3 µm wide, and 0.1 µm thick and includes a 15 µm long, 2 µm thick mass on its end. In some examples, the cantilever is between 100 nm and 10 mm long, 1 nm and 1 mm wide, and 1 nm and 1 mm thick. The cantilever's 102 mass-loaded geometry suppresses the motion of flexural modes above the fundamental frequency. A roughly 50 µm³ particle of $CaF_2$ crystal is glued to the end of the lever and serves as the sample 108. A thin layer of Si/Au (10/30 nm), with Si as an adhesion layer, is evaporated onto the end of the sample to screen electrostatic fields. At T=4.2 K the sample-loaded cantilever has a resonant frequency $v_c$=2.6 kHz and an intrinsic quality factor $Q_0$=44,000, which decreases to $Q_0$=9,000 when approaching the magnetic tip at $B_0$=3 T. The cantilever's 102 spring constant is determined to be k=86 µN/m through measurements of its thermal noise spectrum at several different base temperatures. In some examples, this spring constant is between 10 N/m and 1 µN/m.

The cantilever 102 is mounted in a vacuum chamber (pressure<$1\times10^{-6}$ torr) inside a $^4$He cryostat, which is isolated from environmental vibrations. The motion of the cantilever 102 is detected using laser light focused onto a 10 µm wide paddle 114 near the mass-loaded end and reflected back into an optical fibre interferometer 112. In this experiment, 26 nW of light are incident on the paddle 114 from a temperature-tuned 1550 nm distributed feedback laser diode. The cantilever 102 is damped using feedback to a quality factor of Q=310 in order to increase the bandwidth of the force detection without sacrificing force sensitivity.

Another component of the experiment is the microwire RF source 124, which efficiently produces a strong RF magnetic field $B_1$ for causing nuclear magnetic resonance, and which can do so over a broad bandwidth. In the middle of the microwire structure 120, deposited on its surface, is a 250-nm tall, 200-nm wide FeCo tip 106, in the shape of a truncated cone. This nanomagnetic tip 106 provides the spatial magnetic field gradient required by the MRFM measurement.

During measurement, the sample at the end of the cantilever 102 can be situated less than 100 nm directly above the nanomagnetic tip 106. At such a small spacing, the magnetic tip 106 provides fixed spatial field gradients in excess of $10^5$ T/m. Less than 20 mA passing through the microwire (current density~$10^7$ A/cm²) produce RF $B_1$ fields larger than 4 mT (rotating field) at the position of the sample.

The results of experiments performed with the above apparatus both according to a prior art method and a method according to an embodiment of the invention will now be described with reference to FIGS. 2 and 3.

FIGS. 2a and 2b illustrate the results a prior art method of taking MRFM measurements of a $^{19}$F spin polarization uses adiabatic rapid passage, wherein the microwire is driven with the frequency-sweep sawtooth waveform represented in the inset 206 to FIG. 2a. The frequency of the sawtooth waveform corresponds to twice the resonant frequency of the cantilever ($f_{ci}$) such that nuclei in the resonant slice flip at a frequency that causes the cantilever to resonate. It will be appreciated that the sawtooth waveform is a simplified version of the waveform that was actually used.

In this experiment, a centre frequency of $f_{RFi}$=114 MHz and a peak-to-peak frequency modulation $\Delta f$=750 kHz are used. A superconducting magnet provides the resonant field for $^{19}$F nuclei of $B_0$≈2.8 T. By generating an RF magnetic field with a frequency that is swept through the $^{19}$F resonance frequency twice every cantilever period $T_c$, the longitudinal nuclear spin flips are driven in the sample at the cantilever's resonance frequency. Since the sample is mounted on the end of the cantilever, in the presence of a large enough magnetic field gradient, the spin flips produce a force that drives the cantilever at its resonant frequency. By measuring the amplitude of the cantilever's oscillation at the resonant frequency, the longitudinal component of net spin polarization can be determined. In the present example, this polarization is due to the naturally occurring $\sqrt{N}$ statistical component. The cantilever displacement induced by adiabatic passages is shown in the vibrational spectrum plotted in FIG. 2a.

The narrow band spin signal 202, whose spectral width is inversely proportional to the effective rotating-frame spin lifetime $\tau_m$, sits atop a much broader peak 204 generated by the cantilever's natural thermal vibrations. In FIG. 2b, the spectral density of the cantilever motion illustrated in FIG. 2a is divided by the square of the cantilever transfer-function, to obtain the spectral density of the force experienced by the cantilever. The solid line 210 represents the sum of the thermal noise experienced by the cantilever and the added detection noise.

An embodiment results from the realisation that the illustration in FIG. 2b demonstrates that measuring only one MRFM signal at a time can leave a significant amount of frequency bandwidth unused outside of the measurement bandwidth. That is, the bandwidth of the signal 212 representing the MRFM signal is relatively small in comparison with the usable bandwidth of frequencies in the vicinity of the cantilever's resonant frequency $f_{ci}$, which in this example is 2582 Hz. The usable bandwidth may be considered as the range of frequencies over which forces caused by nuclei flipping can be distinguished from the thermal noise experienced by the cantilever.

One or more embodiments are provided due to a realisation that it is possible to simultaneously measure a plurality of MRFM signals because the bandwidth of multiple individual MRFM signals can fit in the available usable bandwidth of frequencies in the vicinity of the cantilever's resonant frequency without interfering with each other. This will be described with reference to FIG. 3.

FIG. 3 illustrates graphically that for the same general apparatus considered in relation to FIGS. 2a and 2b, an embodiment makes it possible for three MRFM signals 302, 304, 306 that are configured to cause nuclei to flip at slightly different flipping frequencies due to different modulation parameters, to be measured simultaneously for a single cantilever resonance. In addition to the MRFM signals being configured to cause nuclei to flip at slightly different frequencies, each of the MRFM signals also has a different RF frequency such that each of the RF signals causes different resonant slices to be provided.

In this example, the resonant frequency of the cantilever $f_{ci}$ is 2582 Hz, and the three MRFM signals 302, 304, 306 are modulated such that the cantilever is displaced at frequencies of 2574 Hz, 2582 Hz and 2591 Hz. Also, the underlying RF signals have an RF centre frequency of 113 MHz, 114 MHz and 116 MHz respectively.

The optimal lock-in time constant depends on the spin life time, and determines the signal bandwidth which is used for the measurement of each separate spin signal.

In the example shown in FIG. 3, the third spin signal 306, induced by an RF field centred around 116 MHz, is smaller than the other two spin signals 302, 304 because it addresses fewer spins and has significantly lower $\tau_m$ because its associated $^{19}$F spins are closer to the magnetic tip. Because these tips are experiencing a larger field gradient, they are more susceptible to random spin flips caused by magneto-mechanical noise. When the RF signals are generated by mixing an RF signal generated by a digital to analogue converter with an RF carrier frequency of around 90 MHz, as was done in the present example, care should be taken to avoid non-linear inter-modulation products that overlap with the intended RF sweeps.

In other embodiments, the magnetic tip 106 may be supported by the support 102 and the sample 108 may be statically mounted such that the flipping of spins causes the magnetic tip 106 to be displaced. That is, the locations of the sample 108 and magnetic tip 106 as shown in FIG. 1 may be reversed. A sample carrier may be statically mounted or mounted on a moveable support such as the cantilever described herein.

Figure 4:
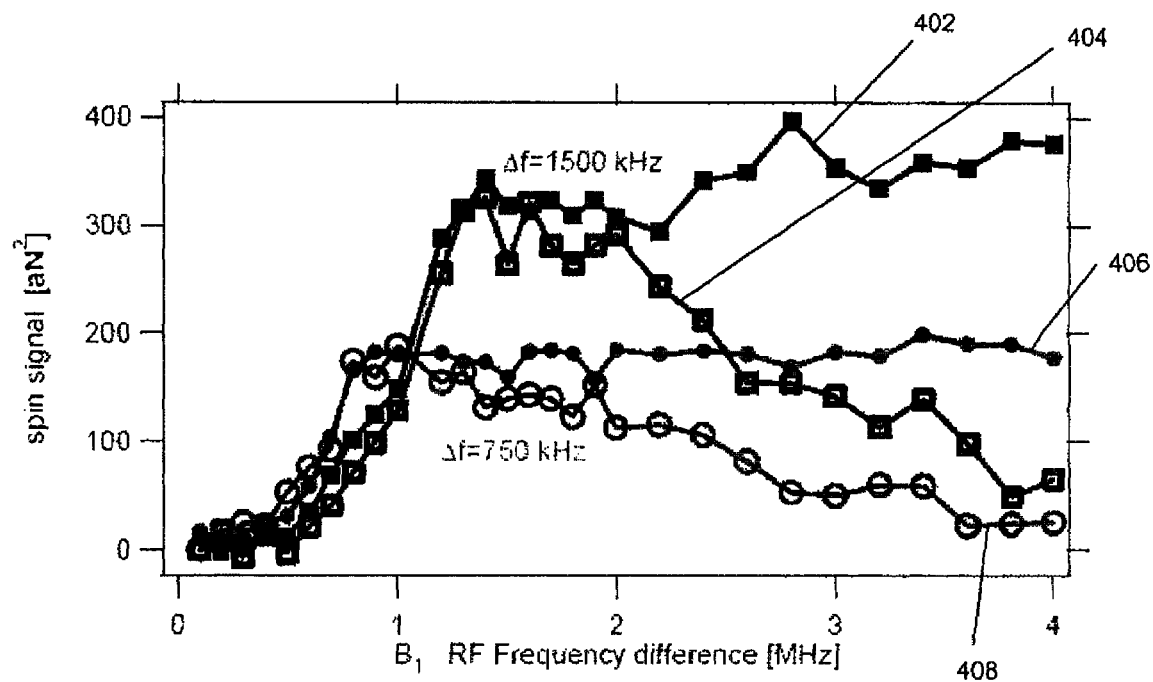
FIG. 4 illustrates graphically the results of MRFM measurements according to an embodiment.

FIG. 4 illustrates how an embodiment can be used to show that two adiabatic rapid passage RF frequency sweeps do not affect the spin signals, as long as they do not overlap. FIG. 4 shows how the spin signal changes for two pairs of RF signals. The first pair of RF signals relates to an example wherein the peak-to-peak frequency deviation ($\Delta f$) is 1500 kHz, and is illustrated by lines 402 and 404 using solid and open square symbols to identify the datapoints. The second pair of RF signals relate to an example wherein the peak-to-peak frequency deviation ($\Delta f$) is 750 kHz, and is illustrated by lines 406 and 408 using solid and open circular symbols to identify the datapoints. The datapoints represented by the solid symbols and open symbols for each of the pairs of RF signals were acquired simultaneously.

As shown in FIG. 4, as the frequency difference between each of the pair of RF signals increases, a frequency difference is reached at which the two resonant slices do not influence each other any more, at which the curves illustrated with solid symbols 402, 406 become independent of the frequency difference. Therefore, for frequency differences above this value, the two spin signals do not influence each other. In this example, the spin signals cease to influence each other at about 0.8 MHz and 1.4 KHz, and this indicates the frequency at which neighbouring resonant slices no longer significantly interfere with each other. That is, the inner surface of a first resonant slice moves away from the outer surface of a second resonant slice.

Figure 5:
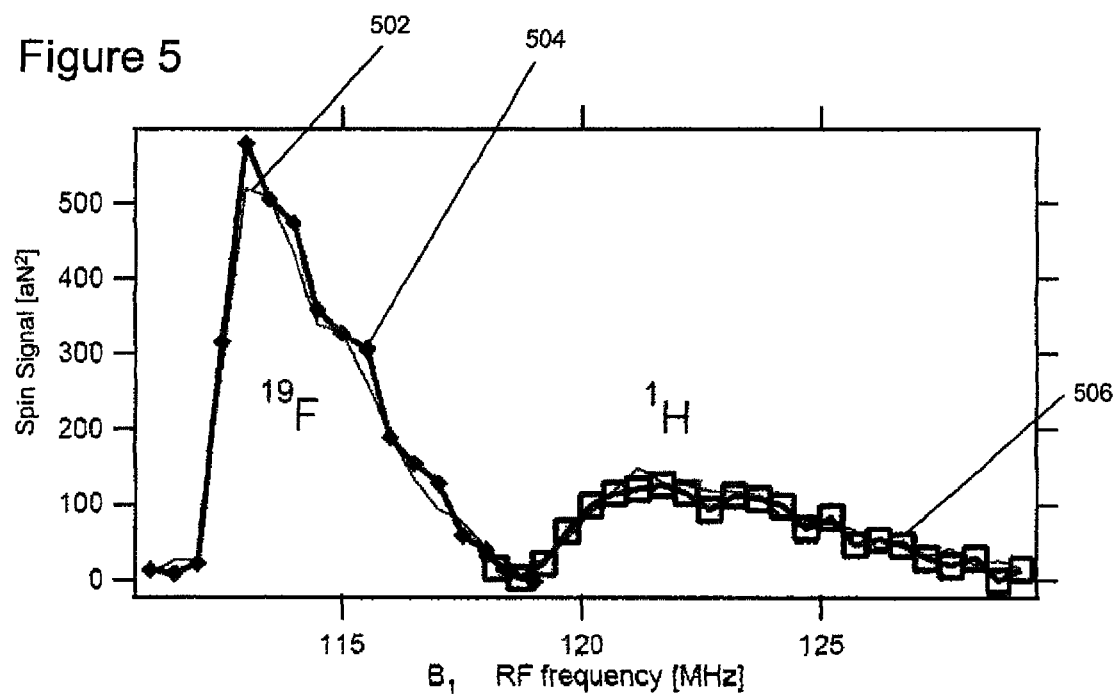
FIG. 5 illustrates graphically the results of MRFM measurements according to an embodiment.

FIG. 5 illustrates how an embodiment can be used to measure the spins generated by different nuclear species simultaneously. In this figure (as in FIG. 4) the datapoints represented by the solid symbols and open symbols were acquired simultaneously.

The line 504 represented by the solid symbols represents measurements that were taken for a resonant slice configured to cause the spin of $^{19}$F nuclei to flip, and the line 506 represented by the open symbols represents measurements that were taken for a resonant slice configured to cause the spin of $^{1}$H nuclei to flip. In this example, the resonant slices of the $^{19}$F and $^{1}$H nuclei are located at the same position, although this does not have to be the case.

The thin line 502 shown behind these datapoints represents data taken using only one RF frequency sweep at a time, and shows that measuring a second atomic species simultaneously does not affect the measurement of the first atomic species as the thin line 502 closely resembles the simultaneously taken data points represented by lines 504 and 506.

It will be appreciated that the forces generated by the flipping of the $^{19}$F and $^{1}$H nuclei are separable because they have different gyromagnetic ratios ($\gamma$), and therefore different nuclear magnetic resonance frequencies. The forces they apply to the cantilever can be distinguished because the flipping frequencies of the $^{19}$F and $^{1}$H nuclei are chosen to be slightly different.

It will be appreciated that the RF signals used to generate the plurality of resonant slices can be configured such that the resonant slices are configured to flip the spin of the same or different nuclei, which may be at the same or different locations in the sample being tested. Furthermore, any modulation scheme can be applied to the RF signals in order to generate the desired flipping frequencies, and can include amplitude modulation, frequency modulation, any other known modulation technique, and any combination thereof, including the use of adiabatic passage and $\pi$-pulses.

Figure 6:
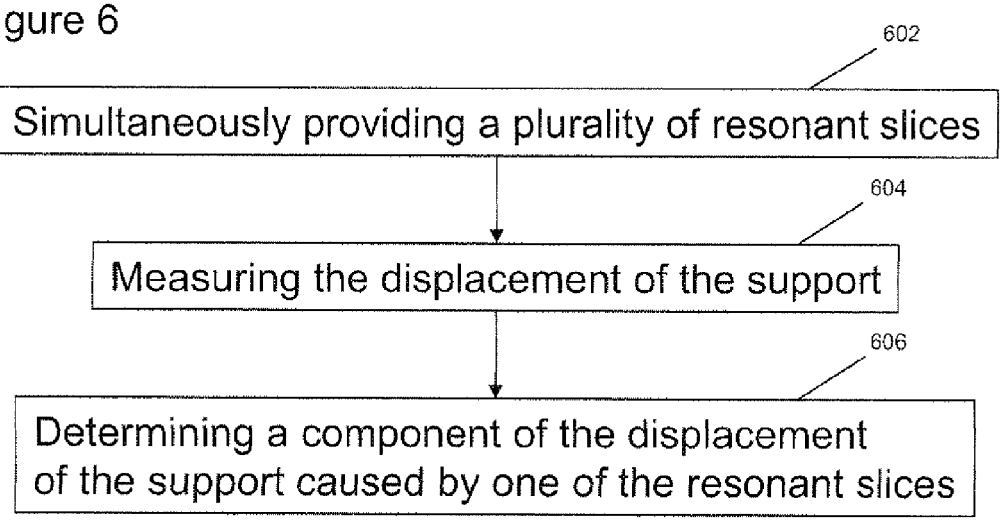
FIG. 6 illustrates schematically a method according to an embodiment.

FIG. 6 illustrates schematically a process flow corresponding to a method of an embodiment. The method is for performing magnetic resonance force detection on a sample supported by a support. In other embodiments, a magnetic field source (or any magnetic field gradient producing structure) may be supported by the support instead of the sample.

The method begins at step 602 by simultaneously providing a plurality of resonant slices. As described herein, a "resonant slice" is a term that can be used to represent a volume that contains a magnetic field that will cause the spin of one or more nuclei in the volume to flip. The frequency of the magnetic field in the volume may be at the nuclear magnetic resonant frequency of a specific nuclear species in order to flip the spins of those nuclei.

The resonant slices are provided simultaneously in as much as at least two resonant slices are generated for the same instance of time. In embodiments that provide $\pi$ pulses, the resonant slices do not necessarily need to be generated for the same instance of time because the $\pi$ pulses can be much shorter than the cantilever period.

As described above, the plurality of resonant slices can be provided simultaneously by providing a microwire with a current signal that comprises a plurality of RF components at different frequencies. In this way, a plurality of resonant slices can be provided at different locations in a sample, and/or one or more of the plurality of resonant slices may cause the spin of different nuclear species to flip, that is, nuclear species with different nuclear magnetic resonant frequencies.

As one or more of the nuclear spins flip, a force is exerted on the support to which the sample is attached/supported. At step 604, the displacement of the support caused by the force of the spins flipping is measured. As described above, particularly, with reference to FIG. 3, the overall displacement of the support consists of a plurality of displacement components at different frequencies, because each of the resonant slices is configured to cause the support to move at a different frequency.

Step 606 involves determining a component of the displacement of the support caused by at least one of the individual resonant slices. In this way, the displacement and force caused by each of the resonant slices can be independently determined so as to build up an image of the nuclei that are present in each of the individual resonant slices. The ability to independently process displacements/forces caused by a plurality of resonant slices at the same time can enable the total processing time to perform magnetic resonance force detection to be reduced when compared with the prior art, and can also make an efficient use of power as the magnetic field that is required to provide each of the resonant slices can be on all of the time, as opposed to time division multiplexing the presence of one or more resonant slices.

In conclusion, it has been demonstrated that it is possible to measure several MRFM signals simultaneously when the effective measurement bandwidth of the cantilever is larger than the signal bandwidth determined by the rotating-frame spin lifetime $\tau_m$. As the detection sensitivity of cantilevers continues to improve, the effective measurement bandwidth of a cantilever with given resonance frequency and quality factor, Q, may get larger and the frequency multiplexing demonstrated herein for a parallel measurement of MRFM signals can prove to be ever more useful as it becomes possible to simultaneously detect an increasing number of MRFM signals.

Further embodiments can be provided wherein the geometry of the cantilever 102 is set such that it has a plurality of resonant frequencies in different dimensions. For example, the cantilever may have a resonant frequency of 2.5 kHz in an x-dimension and a resonant frequency of 2.7 kHz in a y-dimension. In this way, the flipping frequencies of different resonant slices 110 can be set so as to cause the cantilever to move in either the x-dimension or the y-dimension, and modifications to the support displacement measuring sensor can be made accordingly. Such embodiments can further increase the number of MRFM signals that can be simultaneously detected without interfering with each other. It will be appreciated, that in such embodiments, one or more fibre-optic interferometers may be required to detect the displacement of the cantilever 102 in the different dimensions.

Present MRFM systems that are used to determine a three-dimensional image, for example of silicon nano-wires, can take up to two weeks to perform as each of the resonant slices needs to be applied to a sample for a sufficiently long averaging time in order to obtain accurate results. One or more embodiments described herein can reduce the amount of time that it takes to obtain such a structure because a plurality of MRFM measurements can be taken simultaneously. The total time for an imaging operation can be reduced by a factor of n, where n is the number of simultaneous volumes that are addressed.

Embodiments described herein, can make an efficient use of power for generating the resonant slices simultaneously, and can overcome disadvantages associated with Hadamard encoding prior art examples, whereby each of the RF signals needs to generate a particularly high magnetic field $B_1$ in order to make accurate adiabatic inversions of the spins in a relatively thick resonant slice. Also, the resonant slices need to be adjacent to each other in the Hadamard encoding prior art, which is not necessarily the case for embodiments of the present invention.

One or more embodiments described herein, can be more efficient than the prior art, because each of the resonant slices are generated simultaneously, and do not require an increased amount of power such as when the resonant slices are only generated for a proportion of a time period that is time-division multiplexed.

Embodiments of the invention described herein, wherein the cantilever has a plurality of dimensions in which it can be displaced by the flipping of spins, can make efficient use of the resonant slice in more than one dimension. Prior art examples may only utilise the magnetic field across the resonant slice in a single dimension at a time.

While this invention has been particularly shown and described with references to example embodiments thereof, it will be understood by those skilled in the art that various changes in form and details may be made therein without departing from the scope of the invention encompassed by the appended claims.

What is claimed is:

1. A magnetic resonance force detection apparatus, comprising:
    a sample carrier for carrying a sample to be tested;
    a magnetic field source;
    a support for supporting either the sample carrier or the magnetic field source;
    wherein the magnetic field source is configured to expose the sample to a magnetic field by simultaneously providing a plurality of volumes in which the magnetic field is configured to cause spins of one or more nuclei or electrons in the sample to flip, and wherein the flipping of spins exerts a force on the support;
    a support displacement measuring sensor configured to measure displacement of the support resulting from said force exerted on the said support by the flipping of spins of the one or more nuclei or electrons in one or more of the plurality of volumes, and generate a signal representative of said displacement of the support; and
    a processor configured to process the signal representative of the displacement of the support in order to determine a component of the displacement of the support caused by the said flipping of spins of the one or more nuclei or electrons in one or more of the plurality of volumes.

2. The magnetic resonance force detection apparatus of claim 1, wherein the processor is configured to simultaneously process the signal representative of the displacement of the support in order to determine a component of the displacement of the support caused by each of the individual volumes.

3. The magnetic resonance force detection apparatus of claim 1, wherein the magnetic field source comprises a radiofrequency magnetic field source, wherein the radiofrequency magnetic field source is configured to provide a magnetic field comprising the superposition of a plurality of radiofrequency components.

4. The magnetic resonance force detection apparatus of claim 3, wherein each of the plurality of radiofrequency components is configured to cause the magnetic tip to generate a volume in which the magnetic field causes the spins of one or more nuclei or electrons to flip.

5. The magnetic resonance force detection apparatus of claim 3, wherein each of the radiofrequency components is at a frequency that causes magnetic resonance of a spin species in the volume.

6. The magnetic resonance force detection apparatus of claim 3, wherein each of the radiofrequency components is modulated in order to cause the spins to flip at a different frequency.

7. The magnetic resonance force detection apparatus of claim 3, wherein each of the radiofrequency components is modulated in order to cause the spins to flip at a frequency that is at, or close to, the resonance frequency of the support.

8. The magnetic resonance force detection apparatus of claim 1, wherein the support is a cantilever.

9. The magnetic resonance force detection apparatus of claim 1, wherein the support is configured to be displaceable in a plurality of dimensions in response to the flipping of spins.

10. The magnetic resonance force detection apparatus of claim 1, wherein the support displacement measuring sensor comprises a fibre-optic interferometer that is configured to receive laser light reflected from a paddle associated with the support.

11. A method of performing magnetic resonance force detection for a sample using a magnetic force detection apparatus comprising a magnetic field source and a support, wherein either the sample or the magnetic field source is supported by the support, the method comprising:
   simultaneously providing a plurality of volumes in which a magnetic field is provided to cause the spins of one or more nuclei or electrons in the sample to flip, wherein the flipping of spins exerts a force on the support;
   measuring a displacement of the support resulting from said force exerted on the support by the flipping of spins of the one or more nuclei or electrons in one or more of the plurality of volumes, and
   determining a component of the displacement of the support caused by the said flipping of spins of the one or more nuclei or electrons in an individual volume.

12. The method of claim 11, wherein the volumes are distinct volumes that encompass different regions of the sample.

13. The method of claim 11, comprising simultaneously providing two volumes in which a magnetic field is configured to cause the spins of one or more nuclei to flip, wherein:
   a first volume is configured to cause the spins of one or more nuclei of a first nuclear species in the sample to flip; and
   a second volume is configured to cause the spins of one or more nuclei of a second nuclear species in the sample to flip.

14. The method of claim 13, wherein the first and second volumes are at least partially coincident.

15. An apparatus for magnetic resonance force detection, comprising:
   a sample carrier for carrying a sample to be tested;
   a magnetic field source;
   a support for supporting either the sample carrier or the magnetic field source;
   wherein the magnetic field source is configured to expose the sample to a magnetic field by simultaneously providing a plurality of volumes in which the magnetic field is configured to cause spins of one or more nuclei or electrons in the sample to flip, and wherein the flipping of spins exerts a force on the support;
   a support displacement measuring sensor configured to measure displacement of the support resulting from said force exerted on the support by the flipping of spins of the one or more nuclei or electrons in one or more of the plurality of volumes, and generate a signal representative of said displacement of the support; and
   a computer readable medium for storing executable instructions for a data processor to:
   receive the signal representative of the displacement of the support, and to process the signal in order; and
   determine a component of the displacement of the support caused by the said flipping of spins of the one or more nuclei or electrons in one or more of the plurality of volumes.

16. A method of performing magnetic resonance force detection for a sample using a magnetic force detection apparatus comprising a magnetic field source and a support, wherein either the sample or the magnetic field source is supported by the support, the method comprising:
   simultaneously providing a plurality of volumes in which a magnetic field is provided to cause the spins of one or more nuclei or electrons in the sample to flip, wherein the flipping of spins exerts a force on the support;
   measuring a resulting displacement of the support caused by said force exerted by said flipping of spins; and
   operating a data processor to read and execute instructions stored on a tangible medium, the instructions causing the data processor to determine a component of the displacement of the support caused by said flipping of spins of the one or more nuclei or electrons in an individual volume.

* * * * *